United States Patent [19]
McBride et al.

[11] Patent Number: 5,961,800
[45] Date of Patent: Oct. 5, 1999

[54] INDIRECT ELECTRODE-BASED PUMPS

[75] Inventors: Sterling Eduard McBride, Lawrenceville; William Chiang, Monmouth Junction; Paul James Heaney, Skillman; Satyam Choudary Cherukuri, Cranbury, all of N.J.

[73] Assignee: Sarnoff Corporation, Princeton, N.J.

[21] Appl. No.: 08/848,413

[22] Filed: May 8, 1997

[51] Int. Cl.[6] .................................................. G01N 27/26
[52] U.S. Cl. .......................... 204/450; 204/451; 204/600; 204/601
[58] Field of Search .................................. 204/451, 604; 7/453, 601

[56] References Cited

U.S. PATENT DOCUMENTS 3,869,365  3/1975  Sunden .................................... 204/548
5,458,761  10/1995 Kamahori et al. ....................... 204/602

OTHER PUBLICATIONS

Richter et al. ("A micromachined electrohydrodynamic (EHD) pump", Sensors and Actuators A, 29 (1991) 159–168, 1991 month unknown.

*Primary Examiner*—Robert Warden
*Assistant Examiner*—Alex Noguerola
*Attorney, Agent, or Firm*—William J. Burke

[57] ABSTRACT

Provided is an electrode-based pump having source of a pumped fluid, a conduit channel of capillary dimensions connected via a first end to the pumped fluid source and having an outlet at a second end, a piston channel with a first end that intersects the conduit channel, wherein the piston channel allows for periodic inward and outward movement of a piston plug of liquid, two or more electrodes inserted into the piston channel which define an electrode-based pump, wherein the electrode-based pump can be operated to move the piston plug of liquid inward and outward.

17 Claims, 2 Drawing Sheets

INDIRECT ELECTRODE-BASED PUMPS

The present invention is directed to an electrode-based pump that acts directly on a first liquid to effect the pumping of a second liquid.

A number of related applications have been filed on liquid distribution systems that use electrode-based pumps including U.S. application Ser. No.: 08/338,703, filed Nov. 10, 1994 ("A Partitioned Microelectronic Device Array"), now U.S. Pat. No. 5,585,069; 08/455,016, filed May 31, 1995 ("A Partitioned Microelectronic Device Array"), now U.S. Pat. No. 5,593,838; 08/454,771, filed May 31, 1995 ("A Partitioned Microelectronic Device Array"); 08/454,781, filed May 31, 1995 ("A Partitioned Microelectronic Device Array"), now U.S. Pat. No. 5,643,738; 08/454,774, filed May 31, 1995 ("A Partitioned Microelectronic Device Array"), now U.S. Pat. No. 5,681,484; 08/454,772, filed May 31, 1995 ("A Partitioned Microelectronic Device Array"); 08/454,768, filed May 31, 1995 ("A Partitioned Microelectronic Device Array"); 08/556,036, filed Nov. 9, 1995 ("Liquid Distribution System"); 08/469,238, Jun. 6, 1995 ("Electrokinetic Pumping"), now U.S. Pat. No. 5,632,876; 08/556,423, Nov. 9, 1995 ("Electrokinetic Pumping"); 08/645,966, May 10, 1996 ("Electrokinetic Pumping"); 08/483,331, Jun. 7, 1995 ("Method and System for Inhibiting Cross-Contamination in Fluids of Combinatorial Chemistry Device"), now U.S. Pat. No. 5,603,351; 08/730,636, Oct. 11, 1996 ("Liquid Distribution System"); and 08/744,386, Nov. 7, 1996 ("Liquid Distribution System"). These applications are hereby incorporated herein by reference in their entirety. Other related applications have been filed relating to conducting parallel reactions in small volume including U.S. application Ser. Nos.: 08/742,317, filed Nov. 1, 1996 ("Assay System"); and 08/786,956, filed Jan. 23, 1997 ("Parallel Reaction Cassette and Associated Devices"). These applications are hereby incorporated herein by reference in their entirety. U.S. application Ser. No. 08/821,480 (Atty. Docket No. Sarnoff12337), filed Mar. 21, 1997 (McBride, "Balanced Asymmetric Electronic Pulse Patterns for Operating Electrode-based Pumps"), describes a useful way of operating electrode-based pumps to minimize bubble formation at the electrodes, and this application is also hereby incorporated herein by reference in its entirety.

Such systems that are pumped with electrode-based pumps ("electrokinetic" pumps) having no moving parts can be used for example to relay liquids in very small devices to conduct multiple parallel but non-equivalent small-scale syntheses or to conduct multiple small-scale analytical reactions. Some of the fluids that can be useful shuttled with electrode-based pumps are to one degree or another resistant to flow driven by electrode-based pumps. Also, some fluids contain biological materials such as nucleic acids, bacterial or eukaryotic cells, or proteins that can be adversely affected by exposure to the electrode-pumps or the associated electric fields. For example, highly conductive liquids such as aqueous liquids and particularly aqueous solutions containing electrolytes, are most conveniently pumped with electrode-based pumps primarily designed to provide the mode of pumping usually referred to as "electroosmotic" ("EO") pumping. The electrodes of EO pumps are typically situated relatively far apart. However, for ease of designing high density arrangements of electrodes in a high-density microfabricated device for shuttling liquids, it is more convenient to have the electrodes of any one pumping device located adjacently so that the pumps can be integrated in an array configuration that allows localized and selective operation of the pumps. Other liquids, typically of extremely high resistivity, such as carbon tetrachloride, are very resistant to either EO pumping or another form of electrode-based pumping termed "electrohydrodynamic" ("EHD") pumping, which is typically applicable to less conductive liquids. As described in U.S. application Ser. No. 08/556,423 (DSRC 11717A), additives are usefully employed to generate good pumping characteristics in otherwise pumping-resistant liquids. However, it will not always be desirable to add such additives. Accordingly, the present invention provides a device, and related methods for using an electrode-based pump to directly act on a "piston" plug of fluid, which in turn acts on a "pumped" fluid to pump it through a channel or a system of channels.

SUMMARY OF THE INVENTION

The invention provides an electrode-based pump comprising:

a source of a pumped fluid;

a conduit channel of capillary dimensions connected via a first end to the pumped fluid source and having an outlet at a second end;

a piston channel with a first end that intersects the conduit channel, wherein the piston channel allows for periodic inward and outward movement of a piston plug of liquid;

two or more electrodes inserted into the piston channel and comprising an electrode-based pump, wherein the electrode-based pump can be operated to move the piston plug of liquid inward and outward.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DEFINITIONS

The following terms shall have, for the purposes of this application, the meaning set forth below. In particular, for the purpose of interpreting the claims, the term definitions shall control over any assertion of a contrary meaning based on other text found herein:

biological macromolecule
    A "biological macromolecule" is a complex polymer of a class of molecules produced by an organism, such as a nucleic acid, carbohydrate or protein.

biological macrostructure
    A "biological macrostructure" refers to complex organization of molecules such as a cell, an organelle or a virus.

capillary barrier
    A "capillary barrier" is a barrier to fluid flow in a channel comprising an opening of the channel into a larger space designed to favor the formation, by liquid in the channel, of an energy minimizing liquid surface, such as a meniscus, at the opening.

capillary dimensions

"Capillary dimensions" are dimensions that favor capillary flow of a liquid. Typically, channels of capillary dimensions are no wider than about 1.5 mm. Preferably channels are no wider than about 500 μm, yet more preferably no wider than about 250 μm, still more preferably no wider than about 150 μm.

downstream

The "downstream" direction of flow is from a source of pumped liquid to the outlet of a conduit channel.

flow preference

The "flow preference" is direction that a liquid pumps under the influence of an electrode-based pump having two symmetrically situated electrodes each having the same shape, such as rod-shaped electrodes.

pumping limit of an electrode-based pump

The pumping limit of an electrode-based pump acting on a plug of liquid is the point at which the trailing edge of the plug sufficiently reaches one or more of the electrodes so that the electrodes cannot generate further pumping pressure.

DETAILED DESCRIPTION OF THE INVENTION

The present invention is useful for, among other things, providing pumping for the operation of fluidic networks, such as the networks of fluid channels needed to effect complex processes on a small scale. Such networks include those used to convey reagents for synthetic reactions used in combinatorial chemistry.

Figure 1:
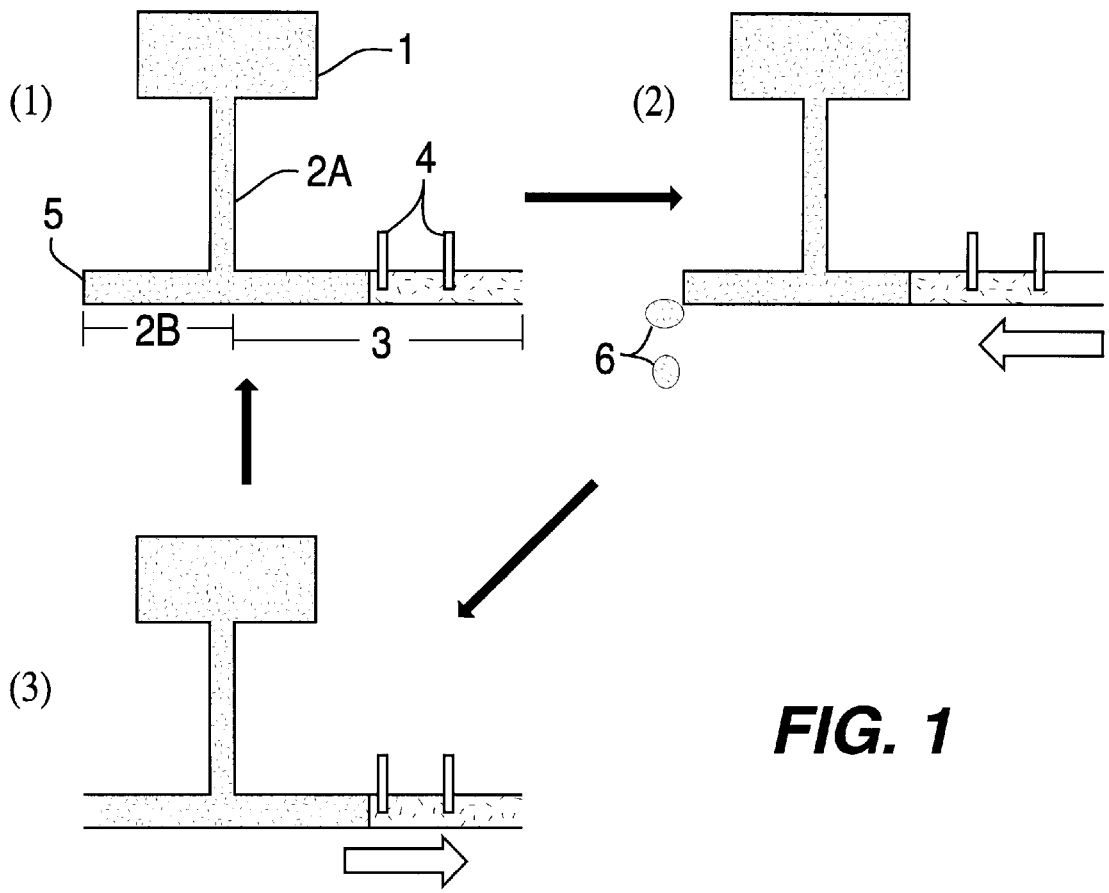
FIG. 1 shows a schematic representing the operation of the pump.

In FIG. 1 is shown an electrode-based pumping system with a reservoir, i.e., source of a pumped fluid 1, a conduit channel 2 having a first segment 2A and second segment 2B, a piston channel 3, an electrode-based pump 4, an outlet 5, and output fluid 6. The three panels indicate three states of operation of the electrode-based pumping system. The open arrows indicate the direction of electrode-based pumping. The first panel shows an arbitrarily designated initial state. The second panel shows an inward stroke of the piston plug of liquid (which plug is indicated by light shading). The third panel shows an outward stroke of the piston plug of liquid, which outward stroke may result in some withdrawal of the pumped fluid (which fluid is indicated by dark shading) from the outlet. In many operations of the electrode-based pumping system, flow from the source of pumped fluid will fill the conduit channel through to the outlet prior to the next inward stroke of the piston plug of liquid. In many cases it will be desirable to avoid having the electrode closest to the pumped fluid contact that pumped fluid, especially where that pumped fluid can generate significant electrolysis at the electrode.

A preferred mode of operation uses electrodes that are spaced apart by from about 25 μm to about 1 mm, and driving voltages from about 25 to about 2,500 volts, more preferably about 100 to about 300 volts.

It should be noted that while the present invention can be used to pump a wide range of pumped fluids, it is preferred to pump liquids. The invention can be used to pump aqueous liquids, particularly aqueous liquids of the type typically applied in biological assays, which often contain relatively high concentrations of electrolytes. For pumping aqueous liquids, the liquid of the piston plug of liquid is preferably a liquid that is sufficiently immiscible with the aqueous liquids anticipated to be pumped so that the pumps can be operated throughout an assay procedure before the piston plugs of liquid need refurbishment. The following solvents are non-limiting examples of solvents useful to form the piston plug of liquid to pump aqueous liquids: toluene, methylene chloride, diethyl ether, chloroform, benzene, hexane, heptane and octane. Some useful solvents, including in some contexts toluene, benzene, hexane, heptane and octane, require the addition of a dopant that increases pumping pressure or efficiency, such as diethyl ether, chloroform, methylene chloride.

To assure that the cycling stroke action of the piston plug of liquid acts to cause a net flow of pumped fluid through the outlet 5, several variables can be adjusted. The source of a pumped fluid 1 can be pressurized, assuring that there is a impetuous to fill the conduit channel when the pump is in its outward stroke. However, the pressurization should not be so great that it drives the piston plug of liquid out of the piston channel. The relative widths of the various channel segments can be adjusted to assure that, during an inward stroke of the piston plug of liquid, outflow through outlet 5 is favored over backflow to the source of pumped fluid 1.

Figure 2:
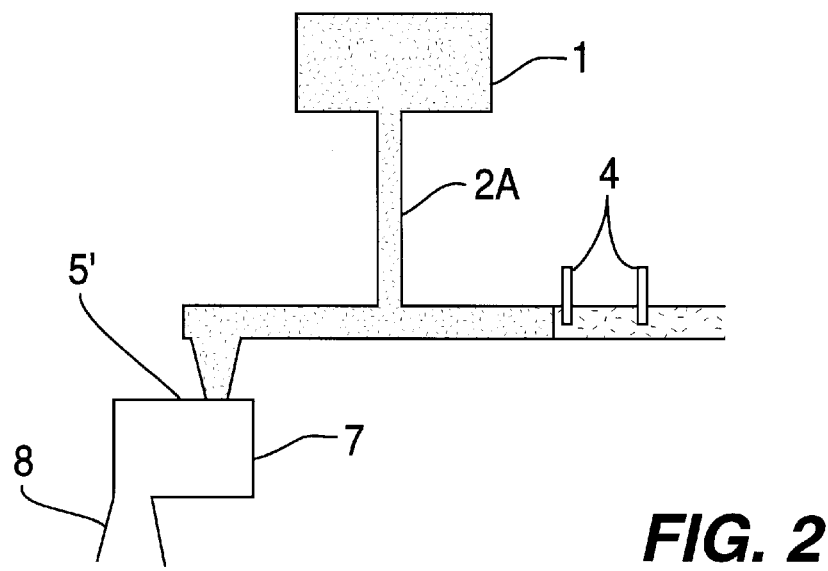
FIG. 2 shows an electrode-based pump of the invention connected to a capillary barrier.

FIG. 2 illustrates that the outlet 5 can be a capillary break 5', which is illustrated as connecting to manifold 8 having drain 9. As described in U.S. application Ser. No. 08/744,386, Nov. 7, 1996 ("Liquid Distribution System"), the capillary break can be reset, if necessary, for instance by flushing manifold 8 with gas. The gas can be introduced for instance via a gas distribution network of channels (not shown).

Figure 3A:
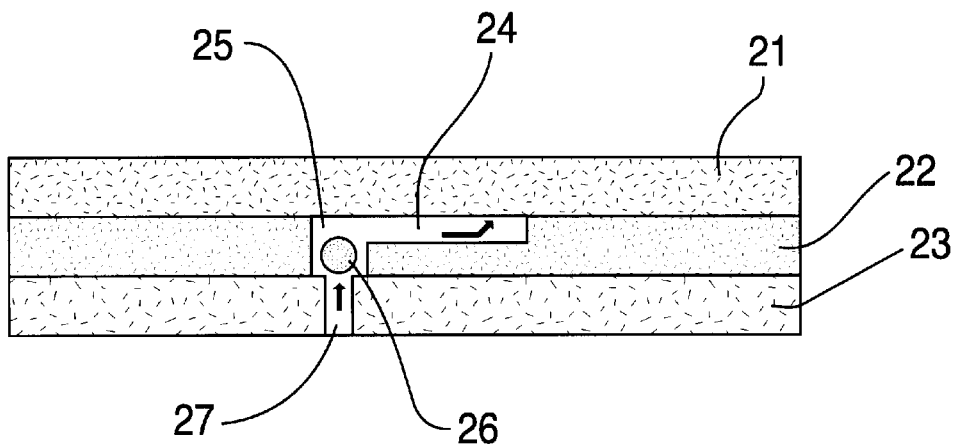
FIG. 3A shows a microfabricated check valve.
Figure 3B:
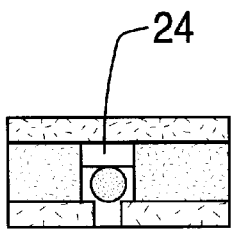
FIG. 3B shows a side view of the check valve.

Check-valves can be incorporated into the channels to assure unidirectional flow. A micromachined check valve is illustrated in FIGS. 3A and 3B. The check valve is formed from three bonded plates: first plate 21, second plate 22 and third plate 23. Where the plates are glass, they can be bonded by an anodic sealing process such as that described in U.S. application Ser. No. 08/745,766, filed Nov. 8, 1996 ("Method of Bonding Glass Plates"). Feeder channel 27 directs fluid to cavity 25, in which sits a round bead 26, such as a glass bead. Feeder channel 27 has a rounded cross-section (not shown), such as results from drilling the channel 27 through third plate 23 by laser ablation. To assure the surface smoothness of the exit of feed channel 27 into cavity 25, during fabrication the upper surface of third plate 23 can be polished following the laser ablation process that forms channel 27. Fluid exits the cavity 25 via exit channel 24. The exit channel 24 has a less-rounded profile, as illustrated in the cross-section of FIG. 3B, such that bead 26 does not seat to block the entrance of exit channel 24 and thereby inhibit fluid flow into exit channel 24.

To maintain the piston plugs of liquid, input ports and optionally reservoirs can be connected to the piston channels. Alternatively, the liquid of the piston plugs can be provided by a secondary fluidic network connecting to multiple piston channels to a reservoir. One method of re-initiating the piston plugs is to overfill the piston channels, and then flush the portions of a fluidic network outside of the piston channels with pumped fluids.

In one embodiment, the position of the interface between a pumped fluid and a piston plug of liquid is monitored with optical detectors, such as a light detector and optionally a light source. Fluctuations in the signal outputted by the detector indicate the transit of a meniscus between the pumped fluid and the piston plug of liquid. Preferably, the signal from at least one optical detector functions to trigger a controller to end an inward or outward stroke of the piston plug of liquid. Preferably, at least two optical detectors are used to monitor the position of a meniscus. Such monitoring can include using a camera, such as one that collects image data in a CCD (Charge-Coupled Device), in which case individual pixels or subsets of pixels aligned with a particular portion of a channel can be considered an optical detector.

Preferably, there is a higher resistance to flow from the source of the pumped fluid to the intersection of the conduit channel with the piston channel than from that intersection to the outlet. Preferably, the liquid source is operable to maintain a hydrostatic pressure, for instance by applying a pressurized blanket of gas, such as an inert gas, above a reservoir of the liquid. Preferably, there is a higher resistance to flow from the source of the pumped fluid to the intersection of the conduit channel with the piston channel than from that intersection to the outlet. Preferably, the outward movement of the piston plug of liquid is effective to draw more fluid from the pumped fluid source than from any liquid situated downstream of the intersection of the conduit channel with the piston channel, and wherein the inward movement of the piston plug of liquid is effective to move sufficient liquid out of the outlet so that there is a net outflow for each paired outward and inward movement of the piston plug of liquid. Preferably, conduit channel comprises one or more check-valves to assure that the pump acts to pump the pumped fluid downstream.

In one embodiment, the invention provides system for conducting multiple aqueous reactions in parallel comprising multiple channels for directing aqueous fluids to multiple reaction chambers, and further comprising multiple electrode-based pumps as described herein.

In another embodiment the invention provides a method of pumping a pumped fluid comprising: providing an electrode-based pump such as described herein with a pumped fluid in the pumped fluid source and a piston plug of liquid in the piston channel; repetitively moving the piston plug of liquid outward (i.e., away from the intersection of the conduit channel with the piston channel) and then inward to create a net downstream motion of the pumped fluid. In one embodiment, the maximum extent one or both of the outward and inward movements of the piston plug of liquid is defined by the pumping limit of the electrode-based pump. Preferably, the liquid of the piston plug of liquid is immiscible with the pumped fluid. In one embodiment, the liquid of the piston plug of liquid is separated from the pumped fluid by a buffer fluid (such as a gas) that is immiscible with both. In another embodiment, the pumped fluid contains a biological macromolecule or a biological macrostructure.

Figure 4:
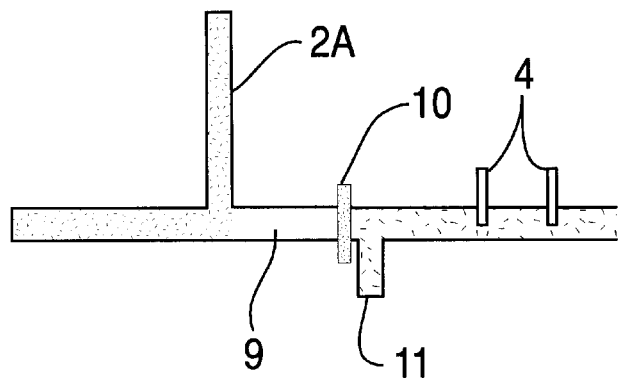
FIG. 4 shows an electrode-based pump of the invention that incorporates a selectively permeable membrane.

In the embodiment where a gas separates the pumped fluid and the piston plug of liquid, a membrane can be positioned in the piston channel, which membrane allows passage of the gas but not the piston plug of liquid, and preferably not the pumped fluid. The membrane thereby acts to delimit at least one of outward or inward strokes of the piston plug of liquid. Accordingly, to create the structure illustrated in FIG. 4, the system is flushed with the separating gas, and the pumped fluid is introduced, trapping separating gas 9 at the appropriate location. Bleed valve 11 is used to introduce piston plug liquid up to the position of membrane 10. Suitable membranes that allow for the passage of gases, but retain liquids include membranes available from Gelman Sciences, Ann Arbor, Mich.

In another embodiment the membrane can be used to remove the gas plug from the system during loading of the piston and pumped fluids. This may be required in a system where a gas gap between piston and pumped fluid is not desirable. In such an embodiment the membrane could be in or coupled to a wall of the channel thereby permitting escape of the gas from the channel.

In one embodiment, the electrode-based pumps are made up of three electrodes, with a shared electrode and a second electrode used to pump in one direction, and the shared electrode and a third electrode used to pump in the other direction. As will be recognized, the use of the shared electrode can facilitate the electronics by which the fluid-driving voltage is reversed to created the oscillating pumping of the invention. For example, with three-electrode pumps two unipolar drivers can be used to drive pumping in the two directions, and such unipolar drivers have fewer components than the bipolar drivers that would needed to reverse the polarity of a two-electrode pump. With fewer components, unipolar drivers can more readily be integrated into a substrate. As described in U.S. application Ser. No. 08/556,423, Nov. 9, 1995 ("Electrokinetic Pumping"), an electrode pair can be designed to create an asymmetric field such that the force acting on either positive or negative charged species is enhanced, such that a liquid in the piston plug can be pumped in the direction opposite its flow preference or more strongly in the direction of its flow preference. Two sets of such asymmetric field-inducing electrodes, which pairs can each include one shared electrode, are a preferred means to drive oscillating pumping. Accordingly, the pumps of the invention can be made up of two such sets of asymmetric field-inducing electrodes. Such pumps can be a first electrode situated along the walls of the channel (e.g., a ring) such that it defines a plane intersecting the fluid channel and a second electrode with a smaller profile or oriented to point in a direction that intersects the plane defined by the first electrode. In a preferred embodiment of this type of pump, the two laterally located electrodes have points oriented towards the shared electrode, which defines a ring. It is believed that the strongest pumping orientations are (1) from the first point electrode to the ring and (2) from the second point electrode to the ring.

In the field of combinatorial chemistry, glass is a preferred substrate in which the channels and pumps are formed. However, other materials such as plastics can be used so long as they have a useful degree of stability against the liquids sought to be pumped. For biological assays, it is anticipated that plastics such as polystyrene, polyethylene, polypropylene, and modified silicone elastomers (such as Sylgard 184 from Corning, Midlands, Mich.).

Without being bound by any particular theory, possible theoretical considerations in electrode-based pumping are set forth in detail in U.S. application Ser. No. 08/556,423, Nov. 9, 1995 ("Electrokinetic Pumping"). At least two types of such electrode-based pumping, i.e., electrokinetic pumping, have been described, typically under the names "electrohydrodynamic pumping" (EHD) and "electroosmosis" (EO). EHD pumping has been described by Bart et al., "Microfabricated Electrohydrodynamic Pumps," *Sensors and Actuators*, A21–A23: 193–197, 1990 and Richter et al., "A Micromachined Electrohydrodynamic Pump," *Sensors and Actuators*, A29:159–168, 1991. EO pumps have been described by Dasgupta et al., "Electroosmosis: A Reliable Fluid Propulsion System for Flow Injection Analysis," *Anal. Chem.*, 66: 1792–1798, 1994.

EO pumping is believed to take advantage of the principle that the surfaces of many solids, including quartz, glass and the like, become charged, negatively or positively, in the presence of ionic materials, such as salts, acids or bases. The charged surfaces will attract oppositely charged counter ions in solutions of suitable conductivity. The application of a voltage to such a solution results in a migration of the counter ions to the oppositely charged electrode, and moves the bulk of the fluid as well. The volume flow rate is proportional to the current, and the volume flow generated in the fluid is also proportional to the applied voltage. Typically, in channels of capillary dimensions, the electrodes effecting flow can be spaced further apart than in EHD pumping, since the electrodes are only involved in applying force, and not, as in EHD, in creating or inducing charges on which the force will act. EO pumping is generally perceived as a method appropriate for pumping conductive solutions.

The present invention is believed to be applicable to all forms of electrode-based pumping, which is often referred to herein as "electrokinetic" pumping. The invention is most preferably applied to electrode-based pumping where the field strength directly acts on liquid components to create pressure, as in EHD and EO. The invention is also applicable to other electrode-based methods, such as traveling wave methods that are believed to work by creating heat convection forces.

The pumps applied in the present invention can be made of simple wire electrodes. Alternatively, where high density arrangements of electrode-based pumps are anticipated, reference can be made to U.S. application Ser. No. 08/554,887, filed Nov. 9, 1995 ("Method of Producing Microelectrical Conduits"), which describes methods of mass producing high density microelectrodes using microfabrication techniques. This application is hereby incorporated into this disclosure by reference in its entirety. These electrodes are formed on plates of dielectric material such as glass, and each such plate is bonded to a plate in which channels have been etched. See U.S. application Ser. No. 08/745,766, filed Nov. 8, 1996 ("Method of Bonding Glass Plates") for plate bonding methodology, which application is hereby incorporated into this disclosure by reference in its entirety.

Driving circuits are set forth in U.S. application Ser. No. 08/469,238, Jun. 6, 1995 ("Electrokinetic Pumping") and U.S. application Ser. No. 08/556,423, Nov. 9, 1995 ("Electrokinetic Pumping")

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. An electrode-based pumping system comprising:
   a source of a pumped fluid;
   a conduit channel of capillary dimensions connected via a first end to the pumped fluid source and having an outlet at a second end;
   a piston channel with a first end that intersects the conduit channel, wherein the piston channel is shaped and configured to allow for periodic inward and outward movement of a piston plug of liquid;
   two or more electrodes inserted into the piston channel to form an electrode-based pump; and
   electrical components adapted to operate the electrode-based pump to move the piston plug of liquid inward and outward by cycling stroke action.

2. The electrode-based pumping system of claim 1, wherein the outlet of the conduit channel comprises a capillary barrier.

3. The electrode-based pumping system of claim 1, wherein there is a higher resistance to flow from the source of the pumped fluid to the intersection of the conduit channel with the piston channel than from that intersection to the outlet.

4. The electrode-based pumping system of claim 1, further comprising a source liquid pressure controller adapted to maintain a hydrostatic pressure in the source of a pumped fluid.

5. The electrode-based pumping system of claim 4, wherein there is a higher resistance to flow from the source of the pumped fluid to the intersection of the conduit channel with the piston channel than from that intersection to the outlet.

6. The electrode-based pumping system of claim 4, wherein the system is adapted so that the outward movement of the piston plug of liquid is effective to draw more fluid from the pumped fluid source than from any liquid situated downstream of the intersection of the conduit channel with the piston channel, and wherein the inward movement of the piston plug of liquid is effective to move sufficient liquid out of the outlet so that there is a net outflow for each paired outward and inward movement of the piston plug of liquid.

7. The electrode-based pumping system of claim 4, wherein conduit channel comprises one or more checkvalves to assure that the pump acts to pump the pumped fluid downstream.

8. The electrode-based pumping system of claim 1, further comprising a membrane, which membrane selectively allows the passage of a gas, positioned in the piston channel between the electrode-based pump and the intersection of the piston channel with the conduit channel.

9. The electrode-based pumping system of claim 1, wherein the electrode-based pump comprises three electrodes including a shared electrode, a second electrode and a third electrode, wherein the shared and second electrode are for pumping the piston plug inward, and the shared and third electrode are for pumping the piston plug outward.

10. The electrode-based pumping system of claim 9, wherein the shape and configuration of (a) the shared electrode and the second electrode and (b) the shared electrode and the third electrode are configured to create a field such that a liquid in the piston plug is pumped in the direction opposite its flow preference or more strongly in the direction of its flow preference.

11. The electrode-based pumping system of claim 1, further comprising a membrane in the capillary channel for allowing venting of gas from the capillary channel.

12. A system for conducting multiple aqueous reactions in parallel comprising multiple channels adapted to directing aqueous fluids to multiple reaction chambers, and further comprising multiple electrode-based pumps according to claim 1.

13. A method of pumping a pumped fluid comprising:
   providing the electrode-based pump of claim 1 with a pumped fluid in the pumped fluid source and a piston plug of liquid in the piston channel;
   repetitively moving the piston plug of liquid outward away from the intersection of the conduit channel with the piston channel, and then inward to create a net downstream motion of the pumped fluid.

14. The method of claim 13, wherein the maximum extent one or both of the outward and inward movements of the piston plug of liquid is defined by the pumping limit of the electrode-based pump.

15. The method of claim 13, wherein the liquid of the piston plug of liquid is immiscible with the pumped fluid.

16. The method of claim 13, wherein the liquid of the piston plug of liquid is separated from the pumped fluid by a buffer fluid that is immiscible with both.

17. The method of claim 13, wherein the pumped fluid contains a biological macromolecule or a biological macrostructure.

* * * * *